United States Patent
Kwan et al.

(10) Patent No.: US 11,877,725 B2
(45) Date of Patent: Jan. 23, 2024

(54) MEDICAL DEVICE AND METHOD OF MANUFACTURE YIELDING MEDICAL DEVICES WITH CONSISTENT SURFACE FEATURES

(71) Applicant: KARL STORZ Imaging, Inc., Goleta, CA (US)

(72) Inventors: Kin Kwan, Goleta, CA (US); Nicolaus Hudson, Santa Barbara, CA (US); Keith Hieber, Santa Barbara, CA (US); Long Nguyen, Goleta, CA (US); Michael Rhodes, Goleta, CA (US)

( * ) Notice: Subject to any disclaimer, the term of this patent is extended or adjusted under 35 U.S.C. 154(b) by 283 days.

(21) Appl. No.: 17/368,295

(22) Filed: Jul. 6, 2021

(65) Prior Publication Data
US 2023/0008104 A1 Jan. 12, 2023

(51) Int. Cl.
| | |
|---|---|
| B22D 18/06 | (2006.01) |
| B22D 21/00 | (2006.01) |
| A61B 1/00 | (2006.01) |
| C22C 21/10 | (2006.01) |
| C25D 1/18 | (2006.01) |
| C25D 11/24 | (2006.01) |

(52) U.S. Cl.
CPC ............ *A61B 1/0011* (2013.01); *B22D 18/06* (2013.01); *B22D 21/007* (2013.01); *C22C 21/10* (2013.01); *C25D 1/18* (2013.01); *C25D 11/246* (2013.01)

(58) Field of Classification Search
CPC .............................. B22D 18/06; B22D 21/007
See application file for complete search history.

(56) References Cited

U.S. PATENT DOCUMENTS

| | | |
|---|---|---|
| 8,512,872 B2 | 8/2013 | Cabot et al. |
| 8,609,254 B2 | 12/2013 | Cabot et al. |
| 8,962,163 B2 | 2/2015 | Shimao et al. |
| 2010/0183869 A1 | 7/2010 | Lin et al. |
| 2014/0004269 A1 | 1/2014 | Barkey |
| 2020/0190649 A1 | 6/2020 | Montes et al. |

FOREIGN PATENT DOCUMENTS

| | | |
|---|---|---|
| CN | 105177669 B | 7/2017 |
| EP | 3042983 A1 | 7/2016 |
| JP | 2004290575 A | 10/2004 |

OTHER PUBLICATIONS

Telias. G., Extended European Search Report, dated Nov. 22, 2022, pp. 1-12, European Patent Office, The Hague.

*Primary Examiner* — Kevin P Kerns
*Assistant Examiner* — Steven S Ha
(74) *Attorney, Agent, or Firm* — David N. Villalpando (57) ABSTRACT

A medical scope device such as an endoscope is produced using a cast aluminum process including a molten casting aluminum alloy including a maximum of 0.2-0.3% Si and at least 5% Zn. The process includes providing an investment casting mold, casting the aluminum alloy in the mold to create a component and removing the mold from the component, post-machining the component to meet a desired specification, and after post-machining the component, performing surface finishing, such as centrifugal barrel finishing (CBF) sufficient to remove impurities on casting surfaces by 2-3 mils, then coating the component with a micro-crystalline aluminum anodic coating of at least 0.5 mil thickness. A medical scope and product-by-process is also provided employing such techniques.

14 Claims, 9 Drawing Sheets

MEDICAL DEVICE AND METHOD OF MANUFACTURE YIELDING MEDICAL DEVICES WITH CONSISTENT SURFACE FEATURES

TECHNICAL FIELD OF THE INVENTION

The invention relates generally to the field of medical devices and more specifically to devices made with casting techniques.

BACKGROUND OF THE INVENTION

Components of endoscopes and other medical scopes are often constructed with milled aluminum blocks which are CNC machined from cold rolled aluminum. The machined parts are anodized to produce a uniform, corrosion resistant finish that can resist the sterilization process often employed with medical scopes. However, when different aluminum stock is employed for different parts such as handgrips and camera housings, often the manufacturing process requires separating the parts during anodization to avoid inconsistent results. In such cases, the process does not produce consistent colors for each part, resulting in the need for the parts to be further color sorted and matched to corresponding parts of a color within an acceptable tolerance. Additionally, the process of CNC machining the parts from aluminum stock is expensive and wasteful.

The use of aluminum casting has, in the past, generally been considered unsuitable for devices such as medical scopes because of the difficulty in producing a uniform anodization layer capable of resisting the medical sterilization process. Further, anodization techniques, when attempted on cast aluminum products, tend to create an oxide layer with irregularities and discoloration.

SUMMARY OF THE INVENTION

It is an object of the invention to improve the manufacture of aluminum medical scope components. It is further an object of the invention to provide reliable techniques for creating medical scope components using casting aluminum alloys which are coated with a micro-crystalline aluminum anodic coating, in which the coating is resistant to medical sterilization processes and has a uniform cosmetic appearance. It is further an object of the invention to provide techniques for controlling the color and cosmetic appearance of components created through investment casting of aluminum to within a desired threshold of color variation. It is further an object of the invention to provide a machining and post-machining process for conditioning components for applying a micro-crystalline aluminum anodic coating with a consistent anodization layer thickness and without discoloration of the oxide layer.

According to a first aspect of the invention, a method of producing a housing for a medical device is provided. The method includes providing a molten casting aluminum alloy including a maximum of from 0.2-0.3% Si and at least 5% Zn. An investment casting mold is provided, and the aluminum alloy is cast in the mold to create a component and removing the mold from the component. Then the component is post-machined to meet a desired specification.

According to some implementations of first aspect, after post-machining the component, a surface finishing, such as by tumbling or centrifugal barrel finishing (CBF) is performed sufficient to remove impurities on casting surfaces by at least 2 mils, preferably 2-3 mils.

According to some implementations of first aspect, the method includes coating the component with a micro-crystalline aluminum anodic coating of at least 0.5 mil thickness.

According to some implementations of first aspect, coating the component with the anodic coating produces a uniform surface color with a maximum color difference (ΔE) of 5.0 on unadorned exterior surfaces of the component.

According to some implementations of first aspect, the casting aluminum alloy is TENZALOY™ 713 comprising 7-8% Zn, 0.2-0.4% Mg, 0.4-1% Cu, and 0.2-0.3% Si.

According to some implementations of first aspect, the casting aluminum alloy is TENZALOY™ 712 comprising 5-6.5% Zn, 0.5-0.65% Mg, 0.4-0.6% Cr, 0.15-0.25% Ti, and 0.2-0.3% Si.

According to some implementations of first aspect, the method further includes, after the surface finishing step, bead blasting the component with a #13 size glass bead media, and the micro-crystalline aluminum anodic coating has a thickness of 0.5-0.9 mils.

According to some implementations of first aspect, the method further includes, after the surface finishing step, bead blasting the component with a blended of 50% #13 and 50% of #10 size glass bead media, and wherein the micro-crystalline aluminum anodic coating has a thickness of 0.5-0.9 mils.

According to some implementations of first aspect, the method further includes, after the surface finishing step, bead blasting the component with a #10 size glass bead media, and wherein the micro-crystalline aluminum anodic coating has a thickness of 1.5-1.9 mils.

According to some implementations of first aspect, the method further includes after the surface finishing step, bead blasting the component with a #220 size aluminum oxide (Corundum) bead media, and wherein the micro-crystalline aluminum anodic coating has a thickness of 1.5-1.9 mils.

According to some implementations of first aspect, the method further includes, after the surface finishing step, bead blasting the component and then performing a bright dip of the component with a solution including phosphoric acid and nitric acid.

According to some implementations of first aspect, the micro-crystalline aluminum anodic coating has a thickness of 1.8 to 2.6 mils.

According to some implementations of first aspect, the micro-crystalline aluminum anodic coating has a thickness of 1.5 to 1.9 mils.

According to some implementations of first aspect, the micro-crystalline aluminum anodic coating has a thickness of 0.5 to 0.9 mils.

According to some implementations of first aspect, the step of casting the aluminum alloy is a lost wax casting method including a water-soluble base molding representing internal negative space within the component. The step of lost wax casting of the aluminum alloy may be performed by vacuum casting.

According to some implementations of first aspect, casting the aluminum alloy in the mold to create a component includes creating at least one temporary cast feature extending from a non-cosmetic surface of the part, and wherein post-machining the component includes attaching a holding fixture to the temporary cast feature to hold the component during at least one portion of the machining.

According to some implementations of first aspect, the method further includes creating a handle for the medical device employing the same process, wherein the housing and handle have the micro-crystalline aluminum anodic coating applied together in the same set of process conditions and in the same electrolytic tank.

According to a second aspect of the invention, a medical scope includes a housing and a scope shaft. The housing is constructed of a cast aluminum alloy including Si at a maximum of 0.3% Si and at least 5% Zn. A micro-crystalline aluminum anodic coating is present on the housing of at least 0.6 mil thickness and having a uniform surface color with a maximum color difference (ΔE) of 5.0 on unadorned exterior surfaces of the housing. The scope shaft is adapted to be attached to the housing.

According to some implementations of the second aspect, the cast aluminum alloy is TENZALOY™ 713 comprising 7-8% Zn, 0.2-0.4% Mg, 0.4-1% Cu, and 0.2-0.3% Si.

According to some implementations of the second aspect, the cast aluminum alloy is TENZALOY™ 712 including 5-6.5% Zn, 0.5-0.65% Mg, 0.4-0.6% Cr, 0.15-0.25% Ti, and 0.2-0.3% Si.

According to some implementations of the second aspect, the micro-crystalline aluminum anodic coating has a thickness of 0.5-0.9 mils.

According to some implementations of the second aspect, the micro-crystalline aluminum anodic coating has a thickness of 1.5-1.9 mils.

According to some implementations of the second aspect, a handgrip is attached to the housing, the handgrip constructed of the cast aluminum alloy and having the same micro-crystalline aluminum anodic coating.

According to some implementations of the second aspect, the micro-crystalline aluminum anodic coating does not exhibit a failure mode including discoloration over the specified color difference, an oxidation spot, or a coating failures, over a series of at least 100 sterilization cycles each including cleaning with a cleaning agent having a pH of 4-12 and a plasma sterilization round including at least one minute of hydrogen peroxide plasma.

According to a third aspect of the invention, a product-by-process produces a medical scope housing. The process includes providing a molten casting aluminum alloy including Si at a maximum of 0.3% Si at least 5% Zn. An investment casting mold is provided and the aluminum alloy is cast in the mold to create the housing. The mold is removed from the housing, and the housing is post-machined to meet a desired specification. After post-machining the housing, the process includes performing surface finishing, such as by tumbling or centrifugal barrel finishing (CBF) sufficient to remove impurities on casting surfaces by at least 2 mils, preferably 2-3 mils. Then the housing is coated with a micro-crystalline aluminum anodic coating of at least 0.6 mil thickness.

According to some implementations of the third aspect, the casting aluminum alloy is TENZALOY™ 713 including 7-8% Zn, 0.2-0.4% Mg, 0.4-1% Cu, and 0.2-0.3% Si.

According to some implementations of the third aspect, the casting aluminum alloy is TENZALOY™ 712 including 5-6.5% Zn, 0.5-0.65% Mg, 0.4-0.6% Cr, 0.15-0.25% Ti, and 0.2-0.3% Si.

According to some implementations of the third aspect, the process further includes, after the surface finishing step, bead blasting the component with a #13 size glass bead media, and wherein the micro-crystalline aluminum anodic coating has a thickness of 0.5-0.9 mils.

According to some implementations of the third aspect, the process further includes, after the surface finishing step, bead blasting the component with a blend of 50% #13 and 50% of #10 size glass bead media, and wherein the micro-crystalline aluminum anodic coating has a thickness of 0.5-0.9 mils.

According to some implementations of the third aspect, the process further includes, after the surface finishing step, bead blasting the component with a #10 size glass bead media, and wherein the micro-crystalline aluminum anodic coating has a thickness of 1.5-1.9 mils.

According to some implementations of the third aspect, the process further includes, after the surface finishing step, bead blasting the component with a #220 size aluminum oxide bead media, and wherein the micro-crystalline aluminum anodic coating has a thickness of 1.5-1.9 mils.

According to some implementations of the third aspect, the process further includes, after the surface finishing step, bead blasting the housing and then performing a Bright Dip of the housing with a solution including phosphoric acid and nitric acid.

According to some implementations of the third aspect, the micro-crystalline aluminum anodic coating has a thickness of 1.8 to 2.6 mils.

According to some implementations of the third aspect, the process further includes, the micro-crystalline aluminum anodic coating has a thickness of 1.5 to 1.9 mils.

According to some implementations of the third aspect, the process further includes, the micro-crystalline aluminum anodic coating has a thickness of 0.5 to 0.9 mils.

According to some implementations of the third aspect, the micro-crystalline aluminum anodic coating does not exhibit a failure mode including discoloration over the specified color difference, an oxidation spot, or a coating failures, over a series of at least 100 sterilization cycles each including cleaning with a cleaning agent having a pH of 4-12 and a plasma sterilization round including at least one minute of hydrogen peroxide plasma.

According to some implementations of the third aspect, the product-by-process further includes a medical scope handle for the medical device created employing the same process, wherein the housing and handle have the micro-crystalline aluminum anodic coating applied together in the same set of process conditions and in the same electrolytic tank.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

Figure 1:
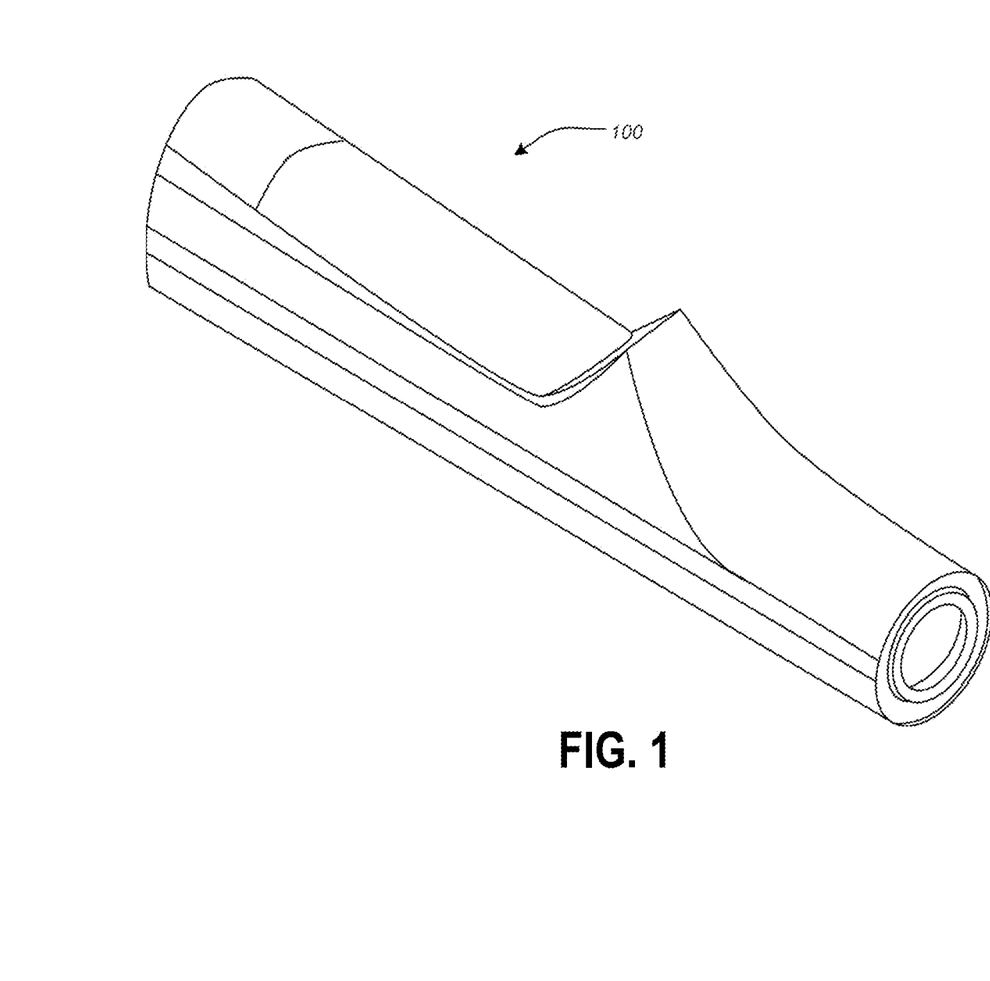
FIG. 1 is a perspective view of a finished handgrip part according to some embodiments.
Figure 2:
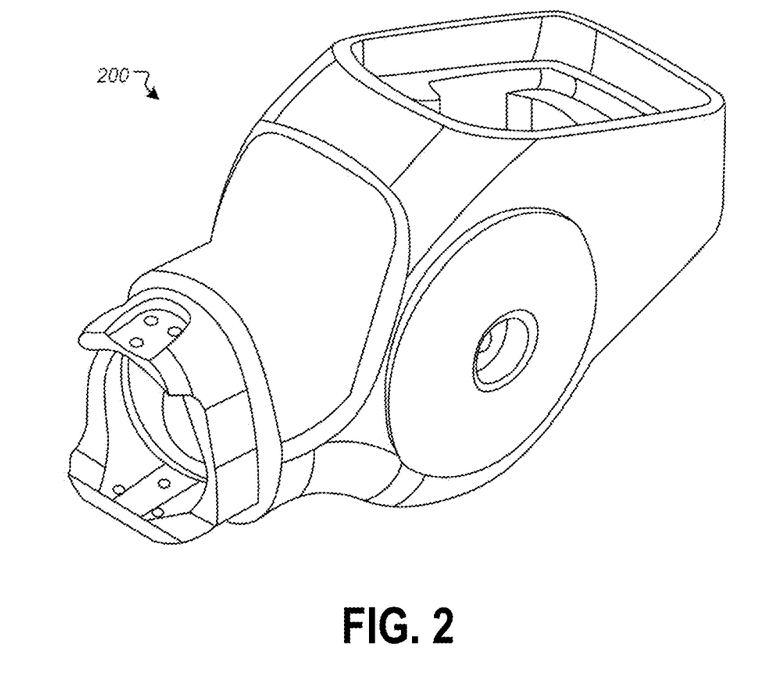
FIG. 2 is a perspective view of a housing part according to some embodiments.

FIG. 1 is a perspective view of a finished handgrip 100 according to some embodiments. FIG. 2 is a perspective view of a housing 200 that will be paired and assembled with handgrip 100 to produce a component of an endoscope according to some embodiments. Prior methods of manufacture include machining handgrip 100 and housing 200 components directly from aluminum stock of different alloys, and individually applying an anodization layer to components. Using the techniques herein, similar parts are produced by investment casting, using a casting aluminum alloy. The components are then assembled into a medical scope including electronics and a scope shaft.

Figure 3:
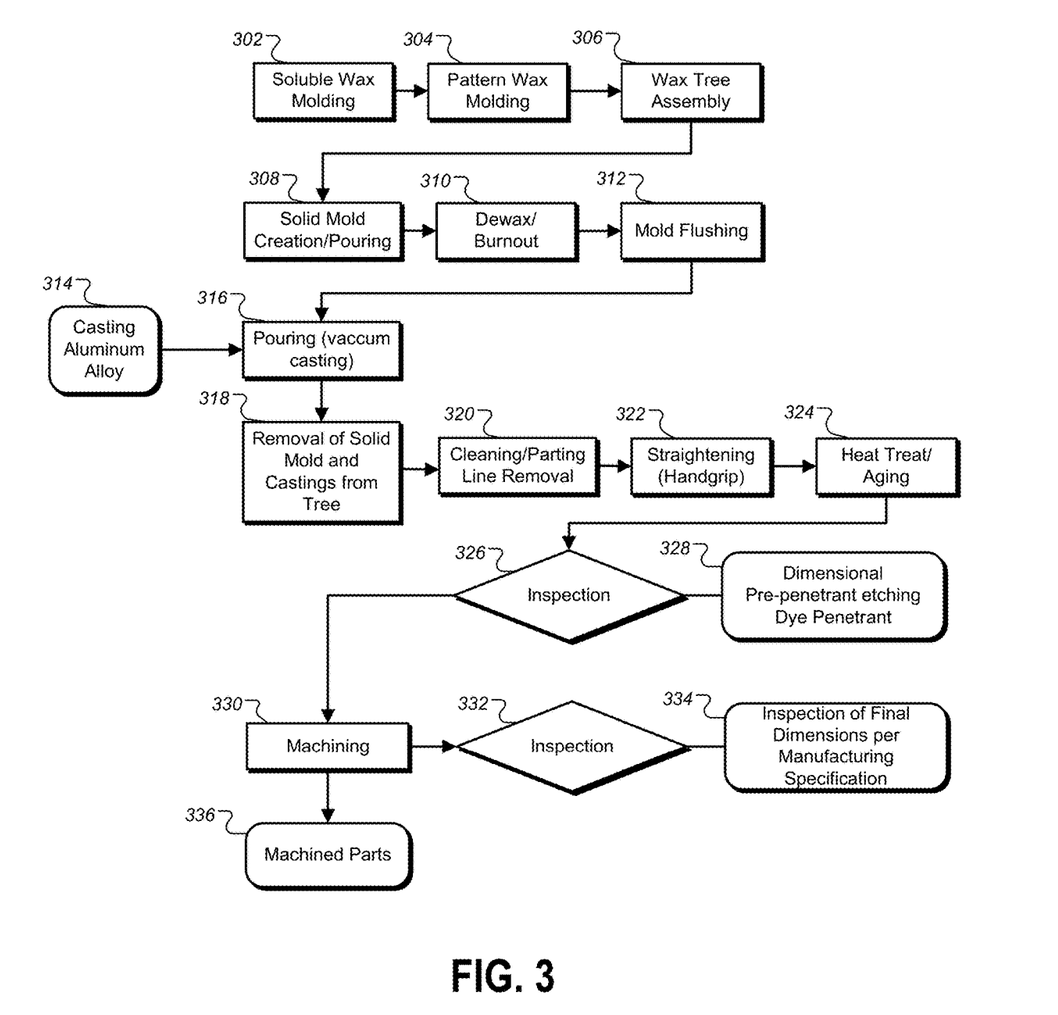
FIG. 3 is a flowchart for a partial process of producing a housing and a handgrip for a medical scope device according to some embodiments.

FIG. 3 is a flowchart for a partial process of producing a housing and a handgrip for a medical scope device according to some embodiments. Generally, the process creates a handgrip and a housing such as a scope camera head for a medical scope.

At block 302, a water-soluble wax base molding is created, this base represents at least the internal negative space within the parts to be cast. This water-soluble wax base provides support and alignment, and helps to ensure internal tolerances are met in subsequent steps. Additionally, the base moldings may be useful in creation of wax tree assembly, described in a later step. Block 302 may include creating an injection die, and the base wax elements may be created by wax injection into the die. Alternatively, these base wax elements may be machined or produced in any other way known in the art such as 3D printing of wax. At block 304, pattern wax molding is performed to make the set of wax patterns to be used for the parts to be produced, which in preferred embodiments are the housing and the handgrip, although the inventive methods herein may be used to produce any number of elements of an endoscope. Block 304 may include creating an injection die or mold, and the wax patterns may be created by wax injection into the die or mold. As is known in the art, a single mold may be used to create many wax patterns. Block 304 may include forming wax gates to attach the wax moldings to a central tree or sprue. In some embodiments, the process may perform 3D printing of the wax patterns rather than using a solid master mold to create wax patterns, as is also true for the creation of soluble wax base in block 302. In some embodiments of this method, block 302 is unnecessary and not used, particularly with embodiments in which the wax patterns of step 304 are created by 3D wax printing, and the tolerances of the printer meet the required tolerances of the method absent the wax base elements.

At block 306, a wax tree assembly is created by attaching the wax patterns to the central tree. This block also usually included the dissolution of the water-soluble wax base created at block 302. Typically, the water-soluble wax base is removed by exposure to water prior to wax tree assembly, however, it is also possible to assemble an entire tree prior to dissolving the wax base. Typically, separate trees are used for each part, with multiple wax patterns attached to the wax tree by wax connections called gates or sprues, which serve to throttle the direction and flow of the alloy into the void made by the pattern. The gates are preferably designed to attach to each pattern at points away from exterior cosmetic surfaces of the design.

At block 308, solid mold creation is performed in which the tree including the attached wax patterns undergoes a process of investment, wherein the tree of wax patterns is surrounded by a heat tolerant solid substance. This step can be done by any suitable techniques known in the art of lost wax casting, such as plaster investment, wherein the tree is connected to a base and placed within a containing heat resistant flask, and then a liquid investment plaster is poured therein and allowed to dry, or where the tree is dipped in a ceramic slurry to create a ceramic shell around the tree and wax patterns, along with their connecting gates. Block 308 may include a multiple-axis dipping robot, pouring, or other known investment processes. In a preferred process, the ceramic investment mold is allowed to dry, and the process is repeated a number of times until a layered (or laminated) ceramic mold, capable of withstanding the stresses of the casting process, has been built. The desired thickness of the mold depends on product size and configuration requirements.

At block 310, the wax is melted out of the shell. The melting process is typically done in a controlled temperature cycle to melt out the wax, burn off remaining wax, and harden or cure the ceramic shell for use as a mold. This block is typically performed in a burnout-kiln or other appropriate high temperature oven. In addition to cleaning the shell, high-temperature ovens increase the stability and strength of the ceramic cast. Additionally, the investment shell may be brought to a temperature nearer to that of the melting point of an aluminum casting alloy, thereby facilitating the flow of the alloy in a subsequent step. Then, at block 312, the resulting mold is flushed to clean any residual deposits by pouring or injecting a flow of warm water into the cavities, flushing, thereby, any wax ash from the interior of the mold. This process improves the surface quality of the cast piece, minimizing pin holes and pitting that might otherwise be caused by wax ash residue remaining within the mold. At this point the mold is ready for use.

At block 314 a molten casting aluminum alloy is provided for filling the mold. In the current state of the art, casting aluminum alloys are considered unsuitable for most medical devices because the cast parts have surface properties unsuitable for anodization that can withstand the intensive sterilization procedures required for most medical devices, including reusable medical scopes. Further, a micro-crystalline aluminum anodic coating, such as Micralox® coatings (Precision Coating, Inc., Woonsocket, Rhode Island), has not been employed previously for medical scopes as described herein for several reasons. The developer of Micralox and the associated anodization processes for forming micro-crystalline aluminum anodic coatings specifically indicates that cast materials are not good candidates for Micralox coatings because they do not allow the formation of a complete and even anodic film required to attain the expected degree of chemical and corrosion resistance. Further, most anodizing techniques yield very non-uniform, and non-consistent surfaces on cast aluminum pieces due to the presence of different elements, in particular silicon, in these casting alloys. The porosity (air spaces) caused by casting also tends to leave voids which create surface defects unsuitable for anodization. Finally, with prior techniques, the relatively low aluminum-to-other-metals ratio (only the aluminum converts to aluminum oxide) shows as surface defects when anodization, including micro-crystalline aluminum anodization, is employed with casting aluminum alloys.

Faced with these challenges, the present inventors performed extensive research, experimentation, and development to identify a castable aluminum alloy that can meet the requirements of medical scopes, and to create a corresponding casting, finishing, and anodizing process as provided herein in order to yield a consistent anodized surface to withstand medical scope sterilization and meet the cosmetic requirements in the industry. The resulting process includes providing a molten casting aluminum alloy including a maximum of 0.2-0.3% Si and at least 5% Zn at block 314. In some embodiments, the casting aluminum alloy is TENZALOY™ 713 including 7-8% Zn, 0.2-0.5% Mg, 0.4-1% Cu, and 0.2-0.3% Si. In other embodiments, the casting aluminum alloy is TENZALOY™ 712 including 5-6.5% Zn, 0.5-0.65% Mg, 0.4-0.6% Cr, 0.15-0.25% Ti, and 0.2-0.3% Si. The alloys may include other metals, for example, as listed in the ANSI specifications for TENZALOY™ 713 shown in Table 1 below, and TENZALOY™ 712 shown in Table 2 below (compositions are listed by weight).

TABLE 1

Tenzaloy 713 Specification

Aliases

| | |
|---|---|
| ANSI AA NUMBER | 713.0 |
| Common Name | 613 |
| UNS Designation | A07130 |
| Alias | 713 |
| Alias | Tenzaloy |

Specification Composition

| | Minimum | Maximum |
|---|---|---|
| Silicon (Si) | | 0.25 |
| Iron (Fe) | | 1.1 |
| Copper (Cu) | 0.4 | 1 |
| Manganese (Mn) | | 0.6 |
| Magnesium (Mg) | 0.2 | 0.5 |
| Chromium (Cr) | | 0.35 |
| Nickel (Ni) | | 0.15 |
| Zinc (Zn) | 7 | 8 |
| Titanium (Ti) | | 0.25 |
| Other (Total) | | 0.25 |

TABLE 2

Tenzaloy 712 Specification

Aliases

| | |
|---|---|
| ANSI AA NUMBER | 712.0 |
| Common Name | D712.0 |
| UNS Designation | A07120 |
| Alias | 712 |
| Alias | D612 |
| Alias | 40E |

Specification Composition

| | Minimum | Maximum |
|---|---|---|
| Silicon (Si) | | 0.3 |
| Iron (Fe) | | 0.5 |
| Copper (Cu) | | 0.25 |
| Manganese (Mn) | | 0.1 |
| Magnesium (Mg) | 0.5 | 0.65 |
| Chromium (Cr) | 0.4 | 0.6 |
| Zinc (Zn) | 5 | 6.5 |
| Titanium (Ti) | 0.15 | 0.25 |
| Other (Total) | | 0.2 |

Next, at block 316, the process includes casting the aluminum alloy in the mold to create a component. The molten alloy may be poured or pumped into the ceramic mold. In preferred embodiments, vacuum casting is used including applying a vacuum to the mold and introducing the molten aluminum alloy such that the vacuum draws the alloy more completely into the mold. Alternatively, the mold can be placed within a vacuum chamber and the molten material may be fed into the mold from above. The use of a vacuum has the advantage of displacing air bubbles contained in the molten alloy by pulling any air in the mold through small pores in the investment material, through which air, but not molten metal, may pass, as well as avoiding the introduction of further air bubbles during the introduction of the molten metal to the mold. Positive pressure or centrifugal force may instead be used to force the alloy into the mold. Then, the mold is cooled to room temperature or with a suitable controlled cooling process, such as air convection.

At block 318, the mold is removed, and the castings removed from the main sprue. In this block, the shell of the mold is broken away from the cast metal parts, and the parts are separated (typically by cut-off) from the sprue and de-gated.

Next at block 320, the process includes cleaning the cast part and removing lines from casting. Typically, the cast part at this step of the process will exhibit various casting process attributes, such as parting lines, gating remnants, and a rough exterior surface. At block 322, the handgrip part is measured to determine if it is straight enough to meet the desired specification, and if not, straightening is performed on the handgrip part, which may include a straightening fixture and heating. At block 324, the process includes heat treatment and aging of the cast parts.

Then at block 326, the process includes inspection of the part to ensure the dimensions meet specification. If a dye penetrant is to be used, the process may also include pre-penetrant etching as shown at block 328.

For parts that pass inspection, the process next performs machining as shown at block 330. Generally, several features of the desired parts, including the majority of the interface features on the handgrip and housing, are beyond the tolerance capability of investment casting, which are presently around ±0.25 mm for the first inch of the cast feature and ±0.13 mm per inch after the first inch.

Figure 5:
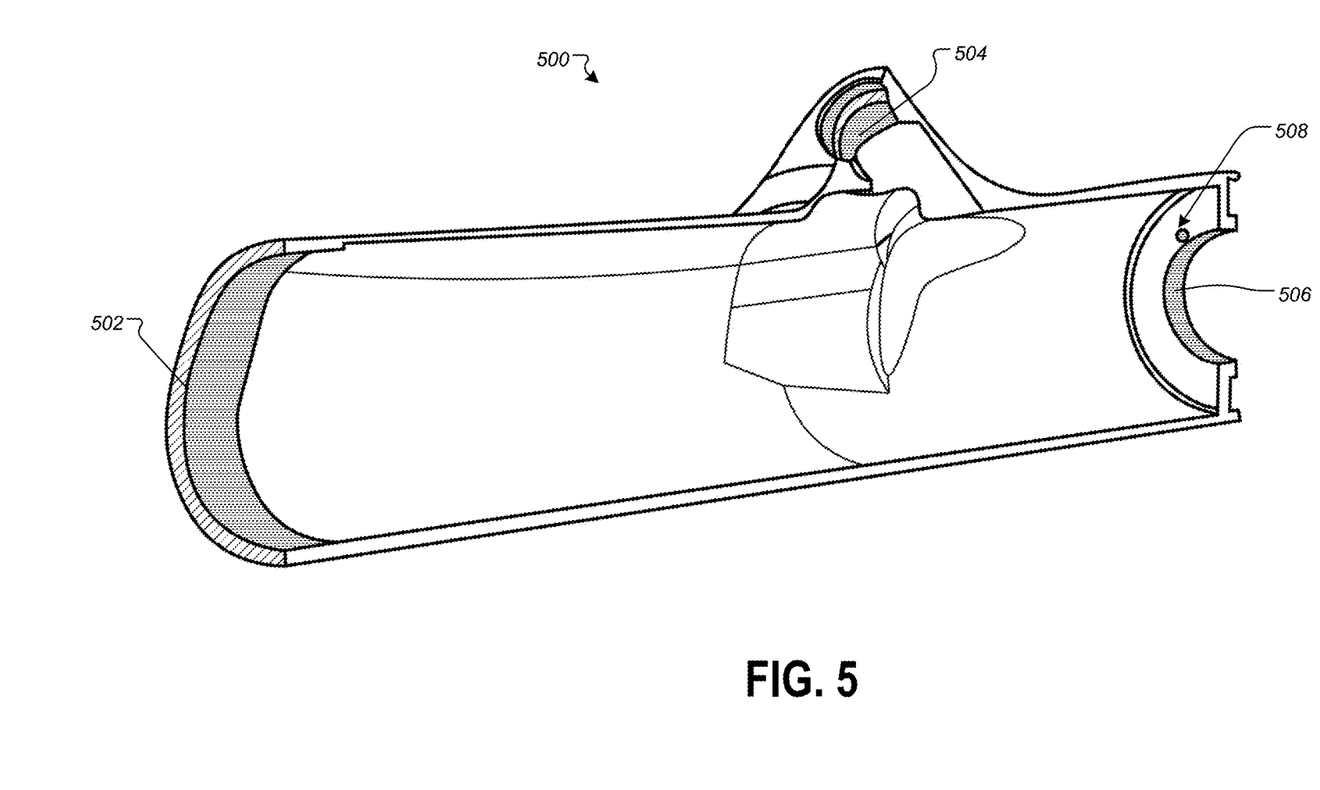
FIG. 5 is a perspective cutaway view of a handgrip part according to one example embodiment.

For the handgrip part, three main areas requiring tighter tolerances due to the fit between mating components will require post machining to achieve the final dimension. As an example, components requiring post-casting machining are shown in the handgrip part 500 of FIG. 5, including the housing interface 502, the valve interface 504, and the shaft adaptor interface 506. In addition to these three main areas, a blind pinhole feature 508, which is used to electrically connect a clock for the internal printed circuit board (PCB) assembly during service of the device, is post machined.

Figure 6:
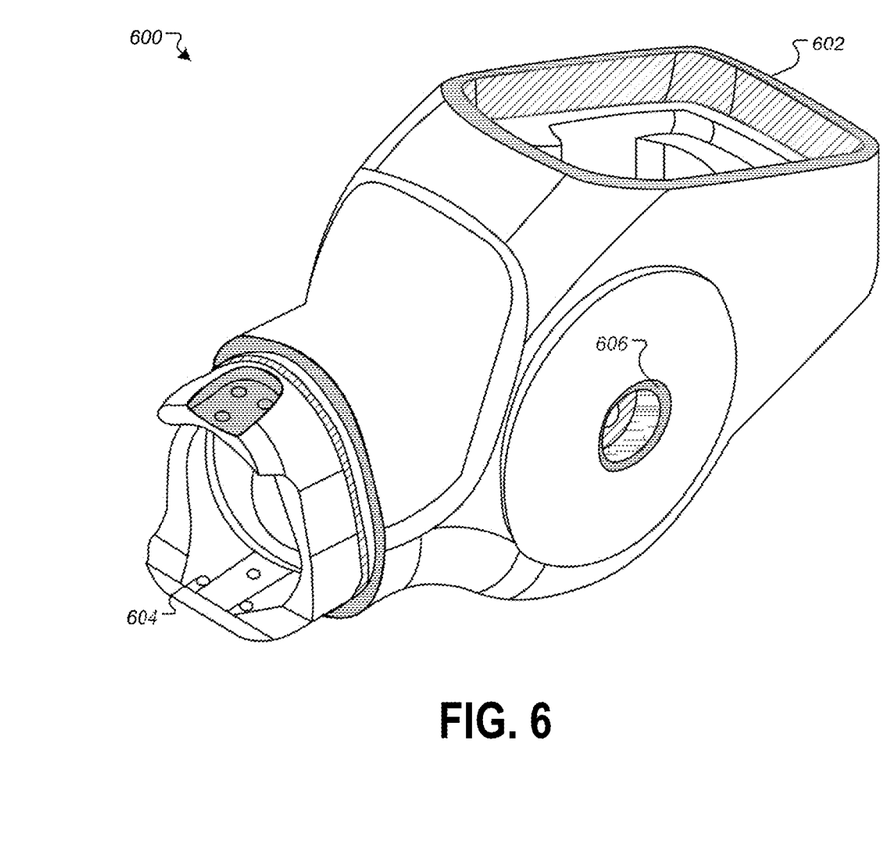
FIGS. 6-8 are different perspective views of a housing part according to one example embodiment.
Figure 7:
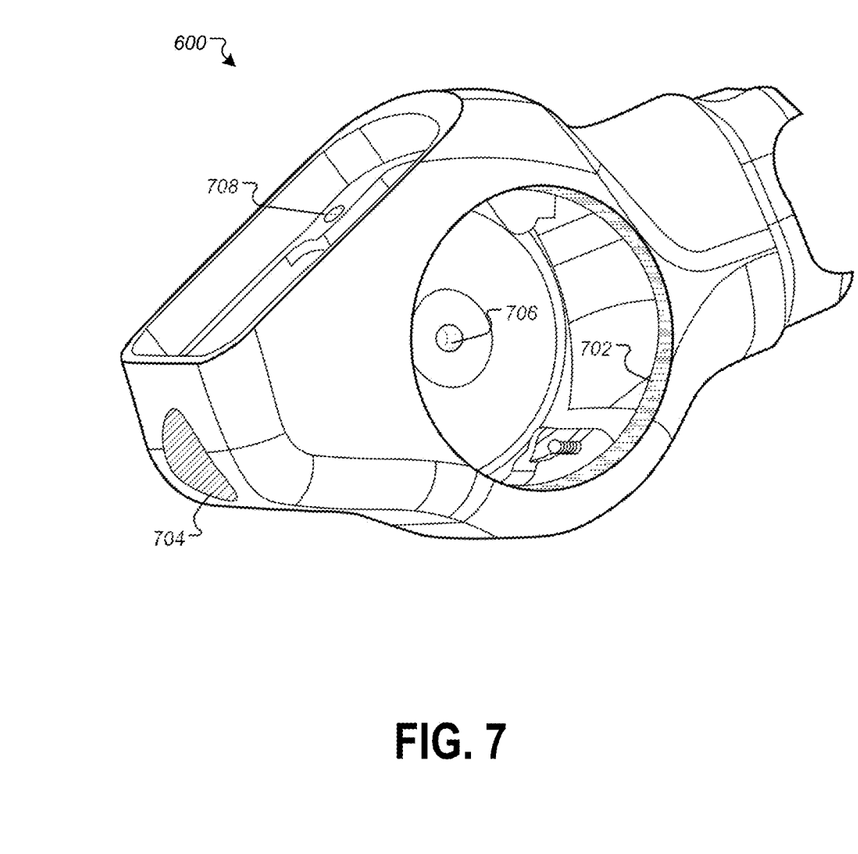
Figure 8:
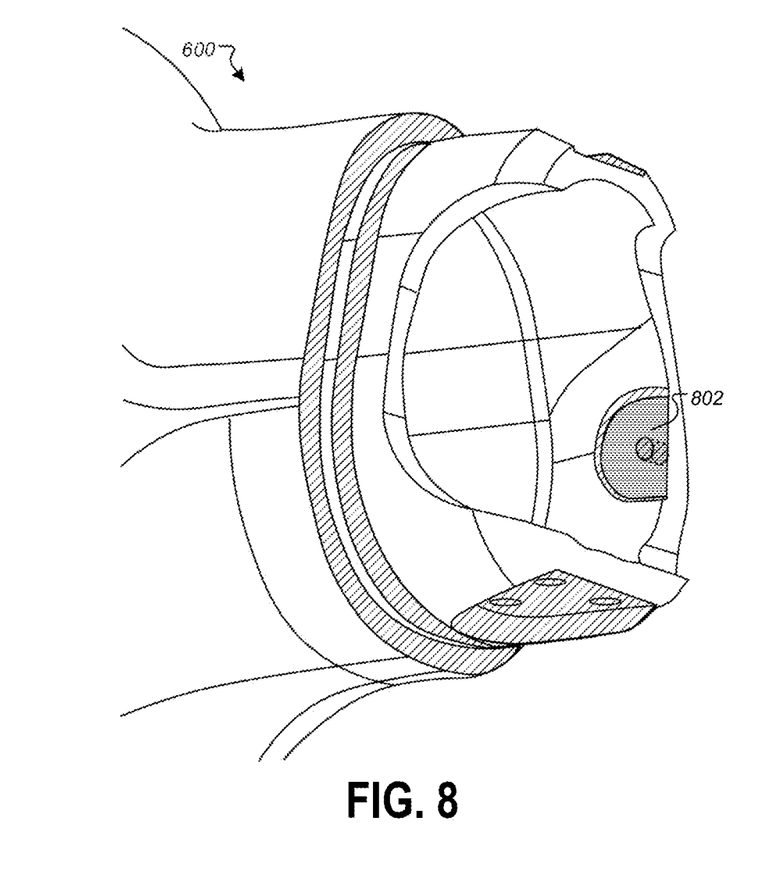

For the housing part, several sealing surfaces which require tight tolerances are machined at block 330, including a button/bezel interface 602 (FIG. 6), an O-ring groove 604 on the handgrip interface, a cap interface 702 (FIG. 7), a cable interface sealing surface 704, and a vent interface 706, 606. These features are important because their function is to seal the assembled device with a reliable barrier that resists corrosion from, or leakage during, the sterilization process. In addition to these features, there are a number of mounting surfaces which are also post machined to achieve the proper fit to the mating components. These features include the top surface and the mounting hole of the bezel interface 708, tapped holes on the upper and lower plate mounts to secure the two plates and PCB assembly, a PCB spacer mount 802 (FIG. 8) used to set the spacing of the PCB inside the handgrip, and the steering disk tab mounting holes used to secure and mount the entire steering mechanism.

Figure 9:
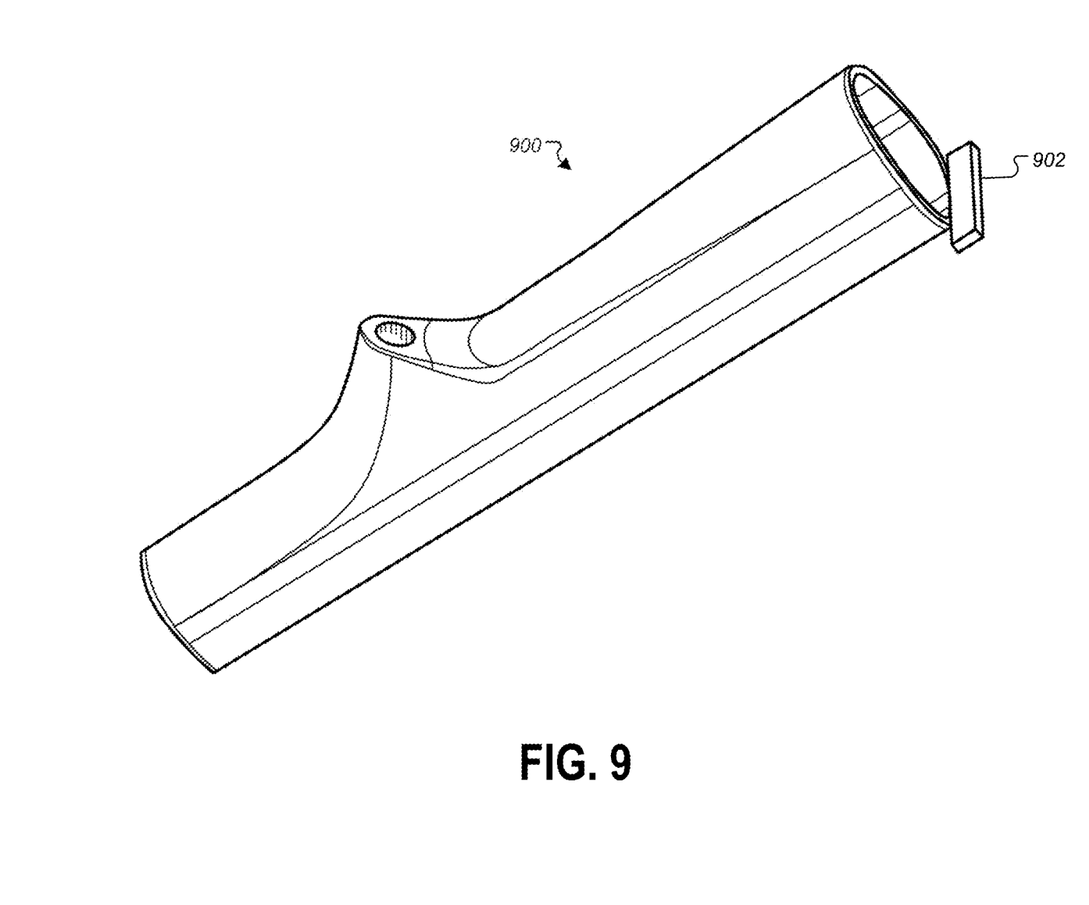
FIG. 9 is a perspective view of a handgrip part showing a temporary cast feature according to some embodiments.

During the machining process, holding fixtures are used to hold the part rigidly for machining. These fixtures are designed to minimize contact with the cosmetic surfaces of the part such that machining of the above features does not result in surface defects such as dents and scratches. In a preferred embodiment, the casting mold and cast parts include temporary cast features which are cast into the parts to provide a place on which holding fixtures attach without causing damage to the cosmetic surfaces of the part. For example, a cast handle part 900 shown in FIG. 9 includes a temporary holding feature 902 which is cast into the part during casting and used to attach the handle to a holding fixture during the machining process. Preferably, this part is attached at a non-cosmetic surface such as the housing interface surface shown holding the temporary holding feature 902 in this example. After the relevant machining steps are performed, temporary holding feature 902 is removed from the cast part, and further machining may be performed on the surface to which temporary holding feature 902 was attached. In one version, the temporary holding feature 902 is attached at an interior surface of the cast part, that is, a surface which is internal to the finished and assembled medical scope. In another version, temporary holding feature 902 is attached at a joining surface such as a surface that will be fit or sealed against another part during assembly. In such case, after temporary holding feature 902 is removed, further machining may be required to smooth the removal location, or, for example, to create threads, grooves, or other features that are employed during assembly to join two adjacent parts, or seal a joint of two adjacent parts.

Following the machining at block 330, the post-machined parts are then inspected at block 332. As shown at block 334, a set of intermediate dimensions are provided in the manufacturing specification for the post-casting part, providing a specified size before anodizing. These dimensions are checked at this point because all related surfaces have been machined, and further changes of dimensions are only due to anodizing. Post-machined parts are provided for anodizing at block 336.

Figure 4:
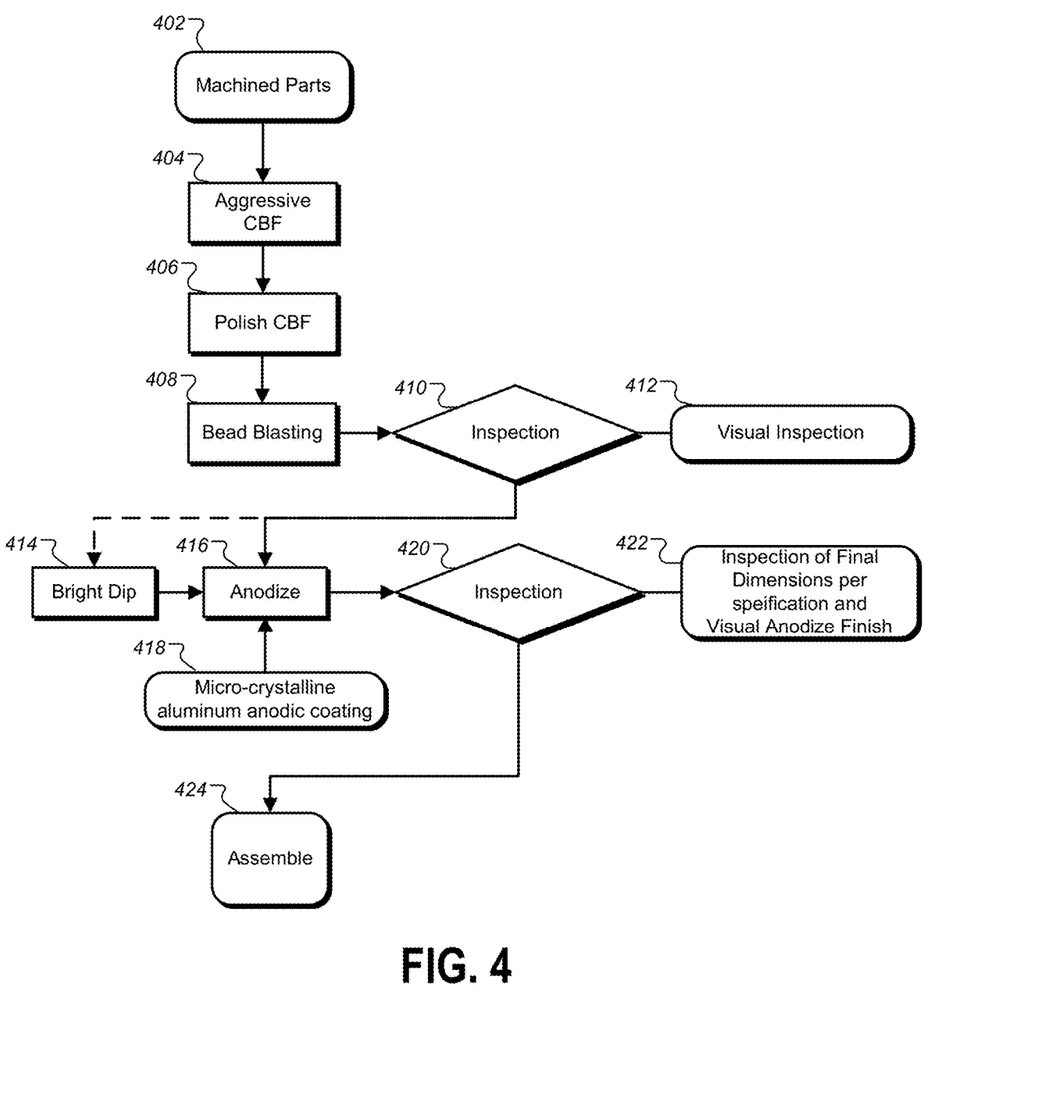
FIG. 4 is a flowchart for a partial process of producing a housing and a handgrip for a medical scope device according to some embodiments.

FIG. 4 is a flowchart for a partial process of producing a housing and a handgrip for a medical scope device according to some embodiments. The process begins with post-machined parts, as shown at block 402, provided by an aluminum casting process such as that of FIG. 3. Other suitable aluminum casting processes may be employed with the depicted process.

At block 404, the process includes performing a surface impurity removal step. This step may include tumbling or other means to remove surface impurities. In a preferred embodiment centrifugal barrel finishing (CBF) is used. The impurity removal step is sufficient to remove impurities on casting surfaces by a desired amount, in general at least 2 mils of material is removed, preferably 2-3 mils. Such a CBF is considered an aggressive CBF in that a high energy tumble is for material removal of the top surface of the alloy to eliminate alloying elements which may have precipitated to the surface of the castings. It was observed during testing that without removing material on the surface of the test parts, the anodize color would be undesirably yellow in color. The cause of this discoloration in the anodize color was determined to be due to the alloying element in TEN-ZALOY™, zinc, being incorporated into the oxide layer formed by the anodize process. In anodization studies directed toward this issue, and several other anodization problems caused by the casting aluminum alloy, it was confirmed that a more aggressive finishing process could reduce and, in most cases, minimized the yellow discoloration in the anodize color.

Next at block 406, a surface finishing technique, such as CBF employing a polishing media to normalize the surface, is performed. This block is important to achieve a consistent surface topography throughout the entire part.

At block 408, a bead blasting is performed to give the part a matte finish. At this block, an appropriate blasting media is selected depending on the desired color of the final finished part. The present inventors have found that surfaces which have a comparatively higher surface roughness generally have a darker anodize color or appearance. However, selecting the bead media roughness does not directly result in a desired color being produced after anodization. Instead, further process steps are paired with particular selections of bead media to produce specific desired colors and surface characteristics. For example, blasting with an aluminum oxide bead media, as discussed below, has been found to provide a relatively high surface roughness, which tends to result in a very dark surface color after anodization. In some embodiments, block 408 includes bead blasting the component with a #13 size glass bead media, or a blended media including approximately 50% #13 size glass bead media and approximately 50% #10 size glass bead media, which has been found to improve covering of micro-pinholes which develop in the casting process. This process is later paired with applying a micro-crystalline aluminum anodic coating (at block 416) having thickness of 0.6-0.9 mils to produce a silver color on the coated surface. In further embodiments, block 408 includes bead blasting the component with a #10 size glass bead media. This process is later paired with a micro-crystalline aluminum anodic coating having thickness of 1.5-1.9 mils at block 416 to produce a Titanium color on the coated surface. In still further embodiments, block 408 includes bead blasting the component with a #220 size aluminum oxide (Corundum) bead media. This process is later paired with a micro-crystalline aluminum anodic coating having thickness of 1.5-1.9 mils at block 416 to produce a dark gray color on the coated surface.

After bead blasting, a visual inspection is performed as shown at blocks 410 and 412. This inspection may be performed manually or with camera inputs. For parts that pass inspection, some embodiments next perform a bright dip (or "brite dip") at block 414 and then proceed to anodization at block 416. Other embodiments do not include a bright dip, and instead go directly to anodization at block 416.

If a bright dip is employed, the process at block 414 may use a standard bright dip including dipping or submersing the component in a solution including phosphoric acid and nitric acid.

At block 418, the process includes coating the component with a micro-crystalline aluminum anodic coating of at least 0.8 mil thickness. Block 418 provides the micro-crystalline aluminum anodic coating, that is applied at block 416 using a process such as that described in U.S. Pat. Nos. 8,512,872 and 8,609,254, owned by Precision Coating Company, Inc. Various methods may be used to perform the anodization. A suitable method of applying such coatings as described by Precision Coating typically includes steps of immersing the anodized aluminum substrate in an electrolytic tank with a first aqueous metal salt solution including at least one metal cationic species to form a partially impregnated aluminum substrate, then immersing the partially impregnated aluminum substrate in an alkaline solution to form a fully impregnated aluminum substrate. The fully impregnated aluminum substrate is immersed in a second aqueous metal salt solution including at least one metal acetate and having a pH in a range of from about 5 units to about 6 units to form a coated anodized aluminum substrate. Preferably, both the housing component and the handle component go through the anodization process together, that is they are placed in the same electrolytic tank for each phase of the micro-crystalline aluminum anodic coating application process. Other suitable methods for applying such a coating may be used.

Various types of micro-crystalline anodic coatings having different thicknesses may be employed at block 416, that each produce variations of a micro-crystalline aluminum anodic coating. In some embodiments, the micro-crystalline anodic coating used has a thickness of 1.8 to 2.6 mils. In other embodiments, the micro-crystalline anodic coating has a thickness of 1.5 to 1.9 mils. In still further embodiments, the micro-crystalline anodic coating used has a thickness of 0.6-0.9 mils. Other variations and other coating thicknesses may, of course, be employed in various embodiments.

Following the anodization, the process includes another inspection at block 420. As shown at block 422, the inspection includes a measurement of final dimensions of the part including coating to check dimensions specified in the manufacturing specification, as well as a visual inspection of the anodize finish. The visual inspection may also include a color difference measurement based on a color sensor measurement or a photographic analysis of the final anodized surface.

Due to the patient contact and sterilization requirements of the medical scope including the housing and handgrip parts, an important design requirement of the handgrip and housing is the integrity of the external cosmetic finish provided by the anodization coating. Both parts must be able to resist repeated cycles of medical sterilization. The sterilization, in one common procedure, includes use of a high pH cleaning agent such as Neodisher® (by Miele, Inc., Princeton, NJ) in cleaning and a strong oxidizing agent (concentrated hydrogen peroxide plasma) such as that provided by the Sterrad® NX and Sterrad 100NX low temperature sterilization machines (by Advanced Sterilization Products, Irvine, CA), or similar products such as the Plasma Low Temperature Sterilizer (by Cisa Production S.r.l. Unipersonale, Lucca, Italy).

Generally, a sterilization cycle for concentrated peroxide plasma includes proceeds as follows. A vaporizer receives the concentrated hydrogen peroxide solution and vaporizes the liquid hydrogen peroxide and water. The condenser condenses the hydrogen peroxide vapor while allowing the water vapor to pass, thereby concentrating the hydrogen peroxide. The condenser vaporizes the hydrogen peroxide and delivers the vapor to a chamber containing the parts to be sterilized. The chamber is then held at a reduced pressure of about 2.5-23.7 Torr for 3-7 minutes. Hydrogen peroxide concentration is typically from 350 mg-s/l to 800 mg-s/l during this time. In some processes, at this point the chamber is then vented to atmosphere through the HEPA filter to cause the hydrogen peroxide to compress and diffuse, driving it into recesses on the parts. Pressure is then reduced to about 600-1500 mTorr, and the condenser is cooled to set point of about 43° C.-57° C. The plasma is then turned on by applying power to create an electric field in the chamber, and the chamber is held in the plasma state for 3-5 minutes, typically 4 minutes. In a Sterrad NX process, plasma power is 500 Watts±10%, with electric power applied at a frequency 50 kHz and 25 ohms of impedance. Then the plasma is turned off and a vent valve opens venting chamber to atmosphere through the HEPA filter. Two such plasma cycles may be used for advanced sterilization. Further, while hydrogen peroxide plasma sterilization is described here, other suitable methods of sterilization may be used, which the anodic coating is preferably able to resist. For example, hydrogen peroxide vapor without plasma, or other chemical sterilization processes that employ a highly-oxidizing agent may be used.

The micro-crystalline anodic coating of the parts at block 416 provides a chemical and mechanical resistance layer on the aluminum surface to withstand the harsh disinfection environment. The present coating methodology has been tested through 100 cycles of Sterrad 100NX and 100 cycles of high pH cleaning with Neodisher without exhibiting failure modes such as oxidation spots, coating failures, or discoloration.

As can be understood from the above description, surface topography, surface morphology, and coating thickness are important factors that effect on the resulting colors of the anodized surface. Specific combinations of these factors are employed to provide desired colors on the cosmetic finish of the final product, as provided in the examples discussed above with respect to block 408. In particular, in the inspection of the anodize finish at block 420, a color difference measurement may be used to verify color specifications. In some embodiments, block 408 includes bead blasting the component with a #13 size glass bead media. This process is later paired with applying a micro-crystalline aluminum anodic coating (at block 416) having thickness of 0.6-0.90 mils to produce a silver color on the coated surface. In further embodiments, block 408 includes bead blasting the component with a #10 size glass bead media. This process is later paired with a micro-crystalline aluminum anodic coating having thickness of 1.5-1.9 mils at block 416 to produce a Titanium color on the coated surface.

In particular, the process combination of bead blasting the component with a #220 size aluminum oxide bead media and anodizing with a micro-crystalline aluminum anodic coating having a thickness of 1.5-1.9 mils produces a dark gray color on the coated surface. This process produces a uniform surface color with a maximum color difference (ΔE) of 5 on unadorned exterior surfaces of the component. The process combination of bead blasting the component with a #13 size glass bead media, and applying a micro-crystalline aluminum anodic coating having thickness of 0.6-0.9 mils produces a silver color on the coated surface with a uniform surface color having a maximum color difference (ΔE) of 5.0 on unadorned exterior surfaces of the component. In preferred embodiments, such a process produces a maximum color difference of approximately 2.25. The process combination of bead blasting the component with a #10 size glass bead media and anodizing with a micro-crystalline aluminum anodic coating having thickness of 1.5-1.9 mils produces a Titanium color on the coated surface with a uniform surface color with a maximum color difference (ΔE) of 5.0 on unadorned exterior surfaces of the component, and in preferred embodiments a color difference of approximately 2.0. The listed color difference specifications are those measured a designated number of sterilization cycles are applied to the finished parts assembled into an endoscope. In particular, parts based on the techniques described herein were tested using the high pH cleaning agent and plasma sterilization process described above for up to 100 cycles.

As such, some embodiments herein provide a product produced with the process above, the product including an anodized coating that does not exhibit a failure mode including discoloration over the specified color difference, an oxidation spot, or a coating failures, over a series of sterilization testing cycles such as 200, 100, 50, 25, or 10 sterilization cycles. Generally cleaning agents can range from low pH to high pH such as from a pH of 4 to a pH of 12. Preferably a high-pH Neodisher cleaning agent is used agent having a pH of approximately 11. Each sterilization cycle includes a plasma sterilization round with hydrogen peroxide plasma of at least one minute as described above. It is noted that the process herein has the advantages that creates a strong micro-crystalline aluminum anodic coating which exhibits such performance over sterilization cycles, while other processes of cast part finishing and applying micro-crystalline aluminum anodic coating may not reliably produce a coating strong enough to resist the intense sterilization process used with medical scopes.

As used herein the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A method of producing a housing for a medical device comprising:
    providing a molten casting aluminum alloy including a maximum of 0.3% Si by weight and at least 5% Zn by weight;
    providing a casting mold including investment material;
    casting the aluminum alloy in the mold under vacuum to create a component and removing the investment material from the component;
    post-machining the cast component to meet a desired specification;
    after post-machining the component, performing a surface finishing sufficient to remove impurities on casting surfaces by at least 2 mils; and
    coating the component with a micro-crystalline aluminum anodic coating of at least 0.5 mil thickness.

2. The method of claim 1, wherein coating the component with the anodic coating produces a uniform surface color with a maximum color difference ($\Delta E$) of 5 on unadorned exterior surfaces of the component.

3. The method of claim 1, wherein the casting aluminum alloy comprises, by weight, 7-8% Zn, 0.2-0.4% Mg, 0.4-1% Cu, and 0.2-0.3% Si.

4. The method of claim 1, wherein the casting aluminum alloy is comprises, by weight, 5-6.5% Zn, 0.5-0.65% Mg, 0.4-0.6% Cr, 0.15-0.25% Ti, and 0.2-0.3% Si.

5. The method of claim 1, further comprising, after the surface finishing, bead blasting the component with a #13 size glass bead media, and wherein the micro-crystalline aluminum anodic coating has a thickness of 0.5-0.9 mils.

6. The method of claim 1, further comprising, after the surface finishing, bead blasting the component with a blend of 50% #13 and 50% of #10 size glass bead media, and wherein the micro-crystalline aluminum anodic coating has a thickness of 0.5-0.9 mils.

7. The method of claim 1, further comprising, after the surface finishing step, bead blasting the component with a #10 size glass bead media, and wherein the micro-crystalline aluminum anodic coating has a thickness of 1.5-1.9 mils.

8. The method of claim 1, further comprising, after the surface finishing step, bead blasting the component with a #220 size aluminum oxide bead media, and wherein the micro-crystalline aluminum anodic coating has a thickness of 1.5-1.9 mils.

9. The method of claim 1, further comprising after the surface finishing step, bead blasting the component and then performing a bright dip of the component with a solution comprising phosphoric acid and nitric acid.

10. The method of claim 1, wherein the micro-crystalline aluminum anodic coating has a thickness of 1.8-2.6 mils.

11. The method of claim 1, wherein the micro-crystalline aluminum anodic coating has a thickness of 1.5-1.9 mils.

12. The method of claim 1, wherein the micro-crystalline aluminum anodic coating has a thickness of 0.5-0.9 mils.

13. The method of claim 1, wherein the step of casting the aluminum alloy is a lost wax casting method including a water-soluble base molding representing internal negative space within the component.

14. The method of claim 13, wherein the step of lost wax casting of the aluminum alloy is performed by vacuum casting.

* * * * *